US012565686B2

(12) United States Patent
Zhao et al.

(10) Patent No.: US 12,565,686 B2
(45) Date of Patent: Mar. 3, 2026

(54) CDI ENHANCED COVID-19 TEST

(71) Applicant: Hackensack Meridian Health, Inc., Edison, NJ (US)

(72) Inventors: Yanan Zhao, Livingston, NJ (US); David S. Perlin, New York, NY (US); Steven Park, Flushing, NY (US)

(73) Assignee: Hackensack Meridian Health, Inc., Edison, NJ (US)

( * ) Notice: Subject to any disclaimer, the term of this patent is extended or adjusted under 35 U.S.C. 154(b) by 383 days.

(21) Appl. No.: 17/100,289

(22) Filed: Nov. 20, 2020

(65) Prior Publication Data

US 2021/0277488 A1 Sep. 9, 2021

Related U.S. Application Data

(60) Provisional application No. 62/989,967, filed on Mar. 16, 2020, provisional application No. 62/985,602, filed on Mar. 5, 2020.

(51) Int. Cl.
*C12Q 1/70* (2006.01)

(52) U.S. Cl.
CPC ....... *C12Q 1/701* (2013.01); *C12Q 2600/158* (2013.01)

(58) Field of Classification Search
None
See application file for complete search history.

(56) References Cited

U.S. PATENT DOCUMENTS 7,776,521 B1 8/2010 Rota et al.

FOREIGN PATENT DOCUMENTS

WO 2004099440 A1 11/2004

OTHER PUBLICATIONS

Corman et al. Detection of 2019 novel coronavirus (2019-nCOV) by real-time RT-PCR. Euro Surveill. 2020;25(3):pii=2000045. Submitted in IDS filed on Nov. 17, 2021.*
20Real-Time RT-PCR Panel for Detection 2019—Novel Coronavirus by CDC. Dated Jan. 24, 2020.*
Victor M Corman et al: "Detection of 2019 novel coronavirus (2019-nCOV) by real-time RT-PCR", Eurosurveillance, vol. 25, No. 3, Jan. 23, 2020 (Jan. 23, 2020), XP055695049, FR ISSN: 1560-7917, DOI: 10.2807/1560-7917.ES.2020.25.3.2000045.
Ishige Taka Yuki et al: "Highly sensitive detection of SARS-COV-2 RNA by multiplex rRT-PCR for molecular diagnosis of COVID-19 by clinical laboratories", Clinica Chimica Acta, Elsevier BV, Amsterdam, NL, vol. 507, Apr. 23, 2020 (Apr. 23, 2020), pp. 139-142, XP086157986, ISSN: 0009-8981, DOI: 10.1 016/J.CCA.2020.04. 023 [retrieved on Apr. 23, 2020].
International Search Report including Written Opinion for PCT/US2021/020664 mailed Jun. 17, 2021; 16 pages.
Li Zhou, et al. Temperature-uniformity On Transverse Flux Induction Heating Applied to Rapid PCR, 4th International Conference on Energy Equipment Science and Engineering, IOP Conf. Series: Earth and Environmental Science 242 (2019), pp. 1-11.
Lars Ullerich, et al., Ultra-fast PCR Technologies For Point-of-care Testing, Journal of Laboratory Medicine, 2017; 41(5); pp. 239-244.
Takara One Step PrimeScriptTM RT-PCR Kit (Perfect Real Time) Instruction manual[online], [Searched on Mar. 19, 2025], Jul. 12, 2018 , Internet: <URL: https://web.archive.org/web/20180712232629/http://catalog.takara-bio.co.jp/PDFS/rr064a_j.pdf>.

* cited by examiner

Primary Examiner — Nianxiang Zou
(74) *Attorney, Agent, or Firm* — Lerner David LLP

(57) ABSTRACT

A detection panel for the universal detection of SARS-like coronaviruses and SARS-CoV-2 viruses and a method for using the detection panel are provided. The detection panel may be known as a Center for Discovery and Innovation ("CDI") detection panel (CDI Enhanced COVID-19 Test) and may also include an additional primer/probe set in the detection panel to detect the human RNase P gene (RP) in control samples and clinical specimens. The detection panel is designed for both universal detection of SARS-like coronaviruses using an E gene (envelope) detection assay, and specific detection of the SARS-CoV-2, using an N2 (nucleocapsid) detection assay.

11 Claims, No Drawings

Specification includes a Sequence Listing.

SEQUENCE LISTING

<160> NUMBER OF SEQ ID NOS: 9

<210> SEQ ID NO 1
<211> LENGTH: 26
<212> TYPE: DNA
<213> ORGANISM: Artificial Sequence
<220> FEATURE:
<223> OTHER INFORMATION: Synthesized

<400> SEQUENCE: 1
acaggtacgt taatagttaa tagcgt                                    26

<210> SEQ ID NO 2
<211> LENGTH: 22
<212> TYPE: DNA
<213> ORGANISM: Artificial Sequence
<220> FEATURE:
<223> OTHER INFORMATION: Synthesized

<400> SEQUENCE: 2
atattgcagc agtacgcaca ca                                       22

<210> SEQ ID NO 3
<211> LENGTH: 26
<212> TYPE: DNA
<213> ORGANISM: Artificial Sequence
<220> FEATURE:
<223> OTHER INFORMATION: Synthesized

<400> SEQUENCE: 3
acactagcca tccttactgc gcttcg                                    26

<210> SEQ ID NO 4
<211> LENGTH: 20
<212> TYPE: DNA
<213> ORGANISM: Artificial Sequence
<220> FEATURE:
<223> OTHER INFORMATION: Synthesized

<400> SEQUENCE: 4
ttacaaacat tggccgcaaa                                                 20

<210> SEQ ID NO 5
<211> LENGTH: 18
<212> TYPE: DNA
<213> ORGANISM: Artificial Sequence
<220> FEATURE:
<223> OTHER INFORMATION: Synthesized

<400> SEQUENCE: 5
gcgcgacatt ccgaagaa                                                   18

<210> SEQ ID NO 6
<211> LENGTH: 23
<212> TYPE: DNA
<213> ORGANISM: Artificial Sequence
<220> FEATURE:
<223> OTHER INFORMATION: Synthesized

<400> SEQUENCE: 6
acaatttgcc cccagcgctt cag                                             23

<210> SEQ ID NO 7
<211> LENGTH: 19
<212> TYPE: DNA
<213> ORGANISM: Artificial Sequence
<220> FEATURE:
<223> OTHER INFORMATION: Synthesized

<400> SEQUENCE: 7
agatttggac ctgcgagcg                                                  19

<210> SEQ ID NO 8
<211> LENGTH: 20
<212> TYPE: DNA
<213> ORGANISM: Artificial Sequence
<220> FEATURE:
<223> OTHER INFORMATION: Synthesized

<400> SEQUENCE: 8
gagcggctgt ctccacaagt                                                 20

<210> SEQ ID NO 9
<211> LENGTH: 23
<212> TYPE: DNA
<213> ORGANISM: Artificial Sequence
<220> FEATURE:
<223> OTHER INFORMATION: Synthesized

<400> SEQUENCE: 9
ttctgacctg aaggctctgc gcg                                             23

CDI ENHANCED COVID-19 TEST

CROSS-REFERENCE TO RELATED APPLICATIONS

The present application is related to and claims priority to U.S. Provisional Patent Application Nos. 62/985,602, filed Mar. 5, 2020, and 62/989,967 filed Mar. 16, 2020, the disclosures of which are incorporated herein by reference.

TECHNICAL FIELD

The present application is related to a detection panel for the universal detection of SARS-like coronaviruses and SARS-CoV-2 viruses and a method for using the detection panel. The detection panel of the present application may be known as a Center for Discovery and Innovation ("CDI") detection panel (CDI Enhanced COVID-19 Test) and may also include an additional primer/probe set in the detection panel to detect the human RNase P gene (RP) in control samples and clinical specimens. The detection panel is designed for both universal detection of SARS-like coronaviruses using an E gene (envelope) detection assay, and specific detection of the SARS-CoV-2, using an N2 (nucleocapsid) detection assay.

BACKGROUND OF RELATED ART

An outbreak of pneumonia caused by a novel coronavirus (SARS-CoV-2) in Wuhan City, Hubei Province, China was initially reported to the World Health Organization (WHO) on Dec. 31, 2019. The emergence and rapid spread of SARS-CoV-2 to numerous areas throughout the world has necessitated preparedness and response in laboratories, as well as health care and other areas of society in general. The availability of specific and sensitive assays for the detection of the virus are essential for accurate diagnosis of cases, assessment of the extent of the outbreak, monitoring of intervention strategies and surveillance studies. The assays being used to detect the virus include an N3 (nucleocapsid) detection assay, which cross-reacts with human nucleic acid, and an N1 (nucleocapsid) detection assay, which was thought to be SARS-CoV-2 specific. However, the N1 assay was found to slightly cross-react with SARS-CoV, which caused inaccurate results.

SUMMARY OF THE PRESENT INVENTION

A method for detecting a novel coronavirus, severe acute respiratory syndrome-Coronavirus-2 (SARS-CoV-2 or COVID-19) in a sample is provided. The method includes collecting a sample suspected of comprising the novel coronavirus, analyzing at least a first portion of the sample for one region in a SARS-CoV-2 nucleocapsid (N) gene using an N2 assay, analyzing at least a second portion of the sample for universal detection of SARS coronaviruses (E) using an E assay; and analyzing at least a third portion of the sample to detect human RNase P (RP) using—human RPP30 (H-RPP30 or RP) assay. The method also includes combining and evaluating results of the N2, E, and RP assays to determine a presence or an absence of the novel coronavirus. The N2 assay is novel coronavirus ("nCoV") specific; the E assay is conversed for all severe acute respiratory syndrome ("SARS") related coronaviruses; and the RP assay is an internal control. The sample is collected from at least one of nasopharyngeal, oropharyngeal, anterior nasal, mid-turbinate nasal, upper respiratory specimens, or blood, urine or stool.

In an another embodiment of the present application, a method for detecting a novel coronavirus, severe acute respiratory syndrome-Coronavirus-2 (SARS-CoV-2 or COVID-19) in a sample includes preparing a master mix for each of a plurality of assays, wherein the assays include: a first assay that is novel coronavirus ("nCoV") specific; a second assay that is conversed for severe acute respiratory syndrome ("SARS") related coronaviruses; and a third assay that is an internal control. In a preferred embodiment, the method also includes loading a quantity of the master mix (e.g., 15 µL) to each of a plurality of wells, wherein the wells are defined by a plate map; and adding a quantity of ribonucleic acid ("RNA") (e.g., 5 µL) to each well as defined by the plate map. The method may also include transferring the sample to a magnetic induction cycler ("mic"), for example, a Mic qPCR cycler (sold by Bio Molecular Systems); and running the mic cycler. The first, second and third assays are an N2 assay, and an E assay, and an RP assay, respectively. The master mix for the RP assay and N2 assay may include: (1) 2× One Step RT-PCR Buffer III; (2) TaKaRa Ex Taq HS (5 U/µl); (3) PrimeScript RT enzyme Mix II; (4) RNase Free dH2O; and (5) Combined Primer/Probe Mix. The master mix for the RP assay and the N2 assay may also include at least: 10 µL/reaction of 2× One Step RT-PCR Buffer III; 0.4 µL/reaction of TaKaRa Ex Taq HS (5 U/µl); 0.4 µL/reaction of PrimeScript RT enzyme Mix II; 3 µL/reaction of RNase Free dH2O; and 1.2 µL/reaction of Combined Primer/Probe Mix. The master mix for the E assay may include: (1) 2× One Step RT-PCR Buffer III; (2) TaKaRa Ex Taq HS (5 U/µl); (3) PrimeScript RT enzyme Mix II; (4) RNase Free dH2O; and (5) E Probe Mix. The master mix for the E assay may also include at least: 10 µL/reaction of 2× One Step RT-PCR Buffer III; 0.4 µL/reaction of TaKaRA Ex Taq HS (5 U/µl); 0.4 µL/reaction of PrimeScript RT enzyme Mix II; 1.8 µL/reaction of RNase Free dH2O; and 2.4 µL/reaction of E Probe Mix.

The method may also include creating a new run using a CDI-COVID 19 assay; selecting a sample type, wherein the sample type is (1) unknown, (2) NTC, or (3) positive control; assigning a group to the sample, wherein the group is (1) N2, (2) E, or (3) RP; and running the mic cycle. The CDI-COVID 19 assay may include thermal cycling conditions. The thermal cycling conditions may include a first stage and a second stage, the first stage being run at 42° C. for 5 minutes for one cycle and the second stage being run at 95° C. for 5 seconds and 58° C. for 20 seconds for 45 cycles.

In another embodiment of the present application, a method for detecting a novel coronavirus, severe acute respiratory syndrome-Coronavirus-2 (SARS-CoV-2 or COVID-19) includes providing a CDI Enhanced COVID-19 test. The CDI Enhanced COVID-19 test may include using a real-time reverse transcription polymerase chain reaction (RT-PCR) test, using a first primer and probe set to detect one region in a SARS-CoV-2 nucleocapsid (N) gene, a second primer and probe set for universal detection of a SARS-like coronaviruses (E), and a third primer and probe set to detect human RNase P (RP) in a clinical sample. The test may be run in a singleplex format or multiplexed into a single reaction and amplification set up. The CDI Enhanced COVID-19 test may also include a no template negative control (NTC) to check for contamination of extraction and assay reagents. The CDI Enhanced COVID-19 test may include two positive controls to verify proper assay set-up and SARS-CoV-2 reagent integrity. The two positive controls may be, for example, a viral genomic RNA for a positive control of a rRT-PCR N2 assay and an E assay, and a DNA positive control for a positive control (RPPC) of an RP assay. The CDI Enhanced COVID-19 test may be run in a single real-time reverse transcription polymerase chain reaction (RT-PCR) test with one positive, one negative and one extraction control included per plate, and each of the clinical samples contain an internal control.

DETAILED DESCRIPTION

The term "sample" as used herein refers to any sample that is taken from a subject (e.g., a human, such as a person suspect of infection) and contains one or more nucleic acids of interest. The term "nucleic acid" as used herein refers to a total nucleic acid including both deoxyribonucleic acid (DNA) and ribonucleic acid (RNA). The term "reaction" as used herein refers to any process involving a chemical, enzymatic or physical action that is indicative of the presence or absence of a nucleic acid of interest. An example of a "reaction" is an amplification reaction such as a polymerase chain reaction (PCR). The term "well" as used herein refers to a reaction at a predetermined location within a confined structure, e.g., a well-shaped vial, cell, or chamber in a PCR array.

As used herein, the term "detection panel" refers to a panel that includes at least two assays to detect the presence or absence of a particular nucleic acid of interest. The term "specimen" as used herein is obtained from nasal wash, aspirate, or a swab in a universal or viral transport media from a subject to be used in the sample. The term "mic cycler" as used herein refers to a mic qPCR cycler as understood by one of ordinary skill in the art.

The detection panel of the present application, also known as SARS-CoV-2 assay or CDI Enhanced COVID-19 Test, is a real-time transcription polymerase chain reaction (RT-PCR) test. The detection panel may be used for presumptive qualitative detection of nucleic acid from the SARS-CoV-2 in upper respiratory specimens (such as nasopharyngeal or oropharyngeal swabs, sputum, lower respiratory tract aspirates, bronchoalveolar lavage, and nasopharyngeal wash/aspirate or nasal aspirate), saliva, serum, urine, and stool samples from individuals suspected of COVID-19. The detection panel may include oligonucleotide primers and probes for detection of the SARS-CoV-2 virus. In particular, the SARS-CoV-2 primer and probe set(s) may be designed to detect RNA from the SARS-CoV-2 in the upper respiratory specimens from patients as recommended for testing by public health authority guidelines. In one embodiment, the oligonucleotide primers and probes may be selected from regions of the virus nucleocapsid (N) gene and the envelope protein (E) gene. Thus, the panel may include a N2 assay and an E assay. In the detection panel, the E assays may detect SARS-like coronaviruses, while the N2 assay may specifically detect SARS-CoV-2. The detection panel may also include an internal control RNase P gene (RP) assay to target human RNase P gene.

The upper respiratory specimens to be used in samples for the panel of the present application may be obtained from nasal wash, aspirate, or a swab in a universal or viral transport media. In particular, the upper respiratory specimens may be obtained from, but is not limited to, a Nasopharyngeal wash/aspirate, Nasal aspirate, Nasopharyngeal swab, Oropharyngeal swab, Anterior nasal swab, Mid-turbinate nasal swab, or tracheal aspirate. Other specimens such as stool, saliva or urine may also be considered as suitable sources for detection of virus.

The results from the detection panel are for the presumptive detection and identification of SARS-CoV-2 RNA in a sample. The SARS-CoV-2 RNA is generally detectable in respiratory specimens during the early and acute phases of infection but can be detected at all stages of disease progression. Positive results are indicative of active infection with SARS-CoV-2 but may not rule out bacterial infection or co-infection with other viruses. The agent detected may not be the sole cause of a respiratory disease.

Negative results from the panel may not preclude SARS-CoV-2 infection and should not be used as the sole basis for patient management decisions. Negative results should be combined with clinical observations, patient history, and epidemiological information to determine patient management.

The panel may be for use by CLIA certified high-complexity laboratories with experience in developing molecular diagnostics and is only for use under the Food and Drug Administration's Emergency Use Authorization.

The CDI Enhanced COVID-19 Test may be used with the Bio Molecular Systems Mic qPCR cycler with micPCR software v2.8.0 or updated version but other testing equipment may be suitable for employing the CDI Enhanced COVID-19 Test.

Table 1 describes the assays and the purpose each has in the detection panel. Table 1 also includes the primer and probes that are included in each assay and their respective function. The sequences of each primer and probe are represented by SEQ ID NOS.: 1-9.

TABLE 1

| Assay | Detection Purpose | Primer/Probe | Function | Sequence (5'-3') |
|-------|-------------------|--------------|----------|------------------|
| E | Conserved detection of SARS-like coronaviruses | E-F | PCR primer | SEQ ID NO. 1 |
| | | E-R | RT & PCR primer | SEQ ID NO. 2 |
| | | E-P | PCR probe | SEQ ID NO. 3 |
| N2 | Specific detection of SARS-CoV-2 | 2019-nCoV_N2-F | PCR primer | SEQ ID NO. 4 |
| | | 2019-nCoV_N2-R | RT & PCR primer | SEQ ID NO. 5 |
| | | 2019-nCoV_N2-P | PCR probe | SEQ ID NO. 6 |
| RP | Internal control, detection of human Rnase-P gene | RP-F | PCR primer | SEQ ID NO. 7 |
| | | RP-R | RT & PCR primer | SEQ ID NO. 8 |
| | | RP-P | PCR probe | SEQ ID NO. 9 |

A method for using the detection panel is also provided. To run a test with the detection panel of the present invention, nucleic acid extraction of the sample may be performed. In one embodiment, the nucleic acid extraction may be achieved with an RNA extraction instrument, for example, a MagNA Pure 24 system (Roche), where total nucleic acids, including both DNA and RNA, may be isolated and purified from a sample, for example, an upper respiratory specimen. After the RNA samples are extracted from the upper respiratory specimen, they should be stored at −80° C. until use.

The assays to be used in the detection panel may be prepared according to the following description. In a detection panel, the RNA samples may be tested in three one-step RT-PCR assays. The three one-step RT-PCR assays may include: 1) a SARS-CoV2 specific N2 assay; 2) all SARS-related coronaviruses conserved E assay, and 3) an internal control RP assay targeting human RNase P gene. The inventors of the present application have found that including all three assays provides improved detection of the presence of the virus in a sample. The assay and plate setup will be described in more detail below.

The RT-PCR is run on mic qPCR cycler (bio Molecular Systems) with the software micPCRv2.8.0. Newer versions of the software will be backward compatible. Other real-time platforms can also be used for detection. When the RT-PCR is run, the probe may anneal to a specific target sequence located between the forward and reverse primers. During the extension phase of the PCR cycle, the 5' nuclease activity of Taq polymerase degrades the probe, causing the reporter dye to separate from the quencher dye, generating a fluorescent signal. With each cycle, additional reporter dye molecules are cleaved from their respective probes, increasing the fluorescence intensity. The software used in the mic qPCR cycler may monitor the fluorescence intensity at each PCR cycle.

A positive control (nCoVPC) may be included in the diagnostic panel. The positive control (nCoVPC) may be a viral genomic RNA, for example, it may be acquired from BEIresources (Cat #NR-52285), and may be used for rRT-PCR N2 and E assays. A viral genomic RNA may also be used in the limit of detection (LoD) evaluation. The viral genomic RNA control may be used at 100 copies per reaction. The positive control in the panel may also include a DNA positive control, such as the CDC SARS-CoV-2 diagnostic panel purchased from Sciencell (Cat #7038-Pos) for RP assay. A no template control (NTC) may also be included in the panel. The NTC may include, but is not limited to, sterile, nuclease-free water. The NTC may be prepared as an aliquot in small volumes, for example each aliquot may be about 1 ml, and there can be at least 50 aliquots prepared. An NTC may also be included to check for contamination that may have occurred during specimen extraction or plate set-up. Both positive controls and NTC must be included in each run.

A human specimen extraction control (HSC) may also be included in the panel. The HSC may be human RNA extract from non-infected samples that can be purchased, for example, from Sciencell (Cat #7038-Hsc). The HSC may be used in each batch of extraction as extraction control.

The nucleic acid should be extracted in each run for target samples, human specimen control and negative extraction control using an RNA extraction instrument. The RNA extraction instrument may be, for example, a MagNA Pure 24 sold by Roche. Additional RNA extraction instruments may be used including QIAamp Viral RNA Mini Kit, EZ1 Virus Mini Kit, and QIAcube sold by QIAGEN or easyMAG sold by NucliSENS. The RNA extracted from the samples, human specimen control and negative extraction control are then used in a real time-PCR (RT-PCR) kit. Any RT-PCR kit can be used to run the extractions.

The preferred materials for use in the diagnostic panel are described in Tables Tables 2 through 5 below. In Table 2, materials for use as the primers and probes in the panel are provided. In Table 3, materials for use as controls in the panel are provided. In Table 4, real time-PCR master mixes for the panel are provided. In Table 5, material for RNA extraction is provided. The expected performance of each control included in the diagnostic panel is shown in Table 6.

TABLE 2

| Assay Primers and Probes | |
| --- | --- |
| Reagent Label | Description |
| SARS-CoV-2_N2 | SARS-CoV-2_N2 Combined Primer/Probe Mix |
| SARS-CoV-2_E | SARS-CoV-2_E Combined Primer/Probe mix |
| RP | Human RNase P Primer/Probe Mix |

TABLE 3

| Control Materials | | | |
| --- | --- | --- | --- |
| Reagent Label | Part # | Description | Notes |
| nCoVPC | Cat#NR-52285 (BEI resources) | The nCoVPC consists of viral genomic RNA extracted from SARS-CoV-2 isolate USA-WA1/2020. nCoVPC will yield a positive result with E and N2 assay in the SARS-CoV-2 Real-Time RT-PCR Diagnostic Panel. | |
| RPPC | Cat#10006626 (IDT-DNA) | The RPPC is the Hs_RPP30 Positive Control (cat#10006626) from IDT-DNA. For use as positive control for RP assay. The RPPC consists of a portion of the RPP30 gene, a single copy gene present in the human genome. | 250 µL (200,000 copies/µL)/ tube in IDTE pH 8.0. |
| HSC | Cat#7038-Hsc (Sciencell) | Human specimen control. For use as an RNA extraction procedural control to demonstrate successful recovery of RNA as well as extraction reagent integrity. The HSC consists of human RNA extract from non-infected samples) purchased from Sciencell (Cat# 7038-Hsc). | |

TABLE 4

| rRT-PCR Enzyme Mastermix Options | | |
| --- | --- | --- |
| Reagent | Quantity | Catalog No. |
| One Step PrimeScript ™ RT-PCR Kit (Perfect Real Time) (Takara) | 100 reactions | RR064A |
| | 500 reactions | RR064B |
| SensiFAST ™ Probe No-ROX One-Step Kit (Bioline) | 100 reactions | BIO-76001 |
| | 500 reactions | BIO-76005 |

TABLE 5

| RNA Extraction | | |
| --- | --- | --- |
| Instrument/ Manufacturer | Extraction Kit | Catalog No. |
| MagNA Pure 24/Roche | MagNA Pure 24 Total Isolation Kit | 96 extractions Product # 07658036001 |

TABLE 6

Expected Performance of Controls Included in the CDI
SARS-CoV-2 Real-Time RT-PCR Diagnostic Panel

| Control Type | External Control Name | Used to Monitor | CDI SARS-CoV-2 E | CDI SARS-CoV-2_N2 | RP | Expected Ct Values |
|---|---|---|---|---|---|---|
| Positive | nCoVPC + RPPC | Substantial reagent failure including primer and probe integrity | + | + | + | <40.00 Ct |
| Negative | NTC | Reagent and/or environmental contamination | – | – | – | None detected |
| Extraction | HSC | Failure in lysis and extraction procedure, potential contamination during extraction | – | – | + | <40.00 Ct |

The internal control, RNase P, may also be detected in the test. All clinical samples should exhibit fluorescence growth curves in the RNase P reaction that cross the threshold line within 40.00 cycles (<40.00 Ct), thus indicating the presence of the human RNase P gene. Failure to detect RNase P in any clinical specimens may indicate:

Improper extraction of nucleic acid from clinical materials resulting in loss of RNA and/or RNA degradation.

Absence of sufficient human cellular material due to poor collection or loss of specimen integrity.

Improper assay set up and execution.

Reagent or equipment malfunction.

If the RP assay does not produce a positive result for human clinical specimens, the result should be interpreted as follows:

If the SARS-CoV-2 E and N2 are positive even in the absence of a positive RP, the result should be considered valid. It is possible, that some samples may fail to exhibit RNase P growth curves due to low cell numbers in the original clinical sample. A negative RP signal does not preclude the presence of CDI SARS-CoV-2 virus RNA in a clinical specimen.

If all SARS-CoV-2 markers and RNase P are negative for the specimen, the result should be considered invalid for the specimen. If residual specimen is available, repeat the extraction procedure and repeat the test. If all markers remain negative after re-test, report the results as invalid and a new specimen should be collected, if possible.

The SARS-CoV-2 markers, E and N2, are also detected in the panel of the present application. When all controls exhibit the expected performance, a specimen is considered negative if both 2019-nCoV markers, E and N2, cycle threshold growth curves do not cross the threshold line within 40.00 cycles (<40.00 Ct) and the RNase P growth curve does cross the threshold line within 40.00 cycles (<40.00 Ct). When all controls exhibit the expected performance, a specimen is considered presumptively positive for CDI SARS-CoV-2 if both markers, E and N2, cycle threshold growth curve crosses the threshold line within 40.00 cycles (<40.00 Ct). In this embodiment, the RNase P marker may or may not be positive as described above, but the SARS-CoV-2 result is still valid.

When the controls exhibit the expected performance and the growth curves for the SARS-CoV-2 markers, E and N2, and the RNase P marker do not cross the cycle threshold growth curve within 40.00 cycles (<40.00 Ct), the result is invalid. The extracted RNA from the specimen should be re-tested. If residual RNA is not available, re-extract RNA from residual specimen and re-test. If the re-tested sample is negative for all markers and RNase P, the result is invalid and a new collection of specimen from the patient should be considered.

When all controls exhibit the expected performance and the cycle threshold growth curve for just N2, but not E, crosses the threshold line within 40.00 cycles (<40.00 Ct), the result is positive.

When all controls exhibit the expected performance and the cycle threshold growth curve for just E, but not N2, crosses the threshold line within 40.00 cycles (<40.00 Ct), the result is inconclusive. Repeat extraction and rRT-PCR.

If HSC is positive for E or N2, then contamination may have occurred during extraction or sample processing. Re-extract specimens and HSC and re-test.

Table 7 lists the expected results for the SARS-CoV-2 rRT-PCR Diagnostic Panel (CDI Enhanced COVID-19 Test) of the present application.

TABLE 7

Expected results for the SARS-CoV-2 rRT-PCR
Diagnostic Panel (CDI Enhanced CoVID-19 Test

| SARS-CoV-2 (N2 gene) | SARS-like coronaviruses (E gene) | RNase P | Interpretation | Report Result | Actions |
|---|---|---|---|---|---|
| + | +/– | +/– | SARS-CoV-2 Detected | POSITIVE | Reported to sender anda ppropriate public health authorities. |
| – | + | +/– | SARS-CoV-2 is Presumptively Positive | PRE-SUMED POSITIVE | Sample is repeated once on extracted RNA. If the repeated result remains "PRESUMPTIVE POSITIVE", additional confirmatory testing may be conducted, if it is necessary to differentiate between SARS-CoV-2 and other SARS-like viruses for epidemiological purposes or clinical management. |

TABLE 7-continued

Expected results for the SARS-CoV-2 rRT-PCR
Diagnostic Panel (CDI Enhanced CoVID-19 Test

| SARS-CoV-2 (N2 gene) | SARS-like corona-viruses (E gene) | RNase P | Inter-pretation | Report Result | Actions |
|---|---|---|---|---|---|
| – | – | + | SARS-CoV-2 Not Detected | NEGATIVE | Reported to sender. Consider testing for other respiratory viruses. |
| – | – | – | Invalid Result | INVALID | Repeat extraction and RT-PCR. If the repeated result remains invalid, consider collecting a new specimen from the patient, if clinically indicated. |

In a particular embodiment, when all controls exhibit the expected performance, as described above, a specimen is considered negative for the SARS-nCoV-2 virus if both SARS-nCoV-2 markers, E and N2, do not cross the cycle threshold growth curve, i.e. the growth curve is less than the threshold curve after about 40.0 cycles and the RNase P growth curve crosses the cycle threshold after less than about 40.0 cycles, the specimen is considered negative. In another embodiment, when all controls exhibit the expected performance, as described above, a specimen is considered to be positive for SARS-nCoV-2 if both SARS-nCoV-2 markers, E and N2, have a cycle threshold growth curve that crosses the threshold line within 40.0 cycles. The RNase P may or may not be positive as described above, but the result of the panel may still be valid.

When the detection panel produces a negative result, the SARS-CoV-2 (2019-nCoV) RNA is not detected in the assays. A negative result may not exclude SARS-CoV-2 infection and should not be used as the sole basis for treatment or other patient management activities. Optimum sample types and timing for peak viral levels during infections caused by SARS-CoV-2 have not yet been determined. Other sample types include gastrointestinal, tissue biopsy, CNS, and urine, which varies by patient population. The possibility of a false negative result may be considered if the patient's recent exposures or clinical presentation suggest that SARS-CoV-2 infection is possible, and diagnostic tests for other causes of illness (i.e., other respiratory illnesses) are negative. Thus, a negative result must be combined with clinical observations, patient history, and epidemiological information. If SARS-CoV-2 infection is still suspected after reviewing the additional information, re-testing should be considered in consultation with infection control or other infectious disease specialists.

When the detection panel produces a presumed positive result, this may indicate an active infection with SARS-CoV-2, but does not exclude bacterial infection and/or co-infection with other viruses. The agent detected may not be the definite cause of disease. A presumed positive result should be combined with clinical observations, patient history, and epidemiological information for patient management decisions. The specimen will be sent for confirmatory testing as required by state and/or federal agencies.

The detection panel may also produce a result that is indeterminate. In an indeterminate result, one cannot reliably determine a result for the specimen due to the inconsistent amplification of all of the required components from the specimen submitted. If clinical observations indicate that a specimen may be infected, an additional sample of the specimen should be submitted for testing.

Validation studies may also be performed during assay development. The validation studies may include, but are not limited to, limit of detection and cross reactivity.

Limit of Detection Studies

To perform the limit of detection study, RNA or an inactivated virus may be spiked into artificial or real clinical matrix (e.g., BAL fluid, sputum, nasopharyngeal swap or oropharyngeal swap, etc.). A 2-3 fold dilution series of three extraction replicates per concentration may be tested, and the final concentration may be confirmed with 20 replicates. The Food and Drug Administration (FDA) defines limit of detection as the lowest concentration at which 19/20 replicates are positive.

Limit of detection (LoD) studies determine the lowest detectable concentration of SARS-CoV-2 at which approximately 95% of all (true positive) replicates test positive. The LoD was determined by limiting dilution studies using characterized samples. The characterized samples were prepared having a known concentration of viral RNA. The analytical sensitivity of the rRT-PCR assays contained in the diagnostic panel of the present application were determined in Limit of Detection studies. The viral genomic RNA (SARS-Related coronavirus 2, isolate USA-WA1/2020) was acquired from BEI resources (Cat #NR-52285) of known titer (RNA copies/µL) spiked into a diluent consisting of nasal swabs suspended in universal transport medium. Samples were extracted using the MagNA Pure 24 instrument. Real-Time RT-PCR assays were performed using the One Step PrimeScript™ RT-PCR Kit (Perfect Real Time) (Takara) (cat #RR064B), and the Bioline SensiFAST Probe No-ROX One-Step Kit on the Bio Molecular Systems mic qPCR cycler according to the CDI SARS-CoV-2 Real-Time RT-PCR Diagnostic Panel instructions for use.

A preliminary limit of detection for the E and N2 assays was determined testing triplicate samples of 3-fold serial dilutions of viral genomic RNA (Cat #NR-52285). A confirmation of the LoD was determined using 10 and 20 copies per reaction of the viral RNA in 20 replicates. The LoD was determined as the lowest concentration where ≥95% (19/20) of the replicates were positive. The results of the limit of detection tests are in Tables 8-12.

TABLE 8

Limit of Detection Confirmation of the CDI SARS-CoV-2
Real-Time RT-PCR Diagnostic Panel using Takara
One Step PrimeScript ™ RT-PCR Kit

| | Targets | | | |
|---|---|---|---|---|
| | SARS-CoV-2 E | | SARS-CoV-2 N2 | |
| RNA Concentration[1] | 4 | 2 | 4 | 2 |
| Positives/Total | 20/20 | 12/20 | 19/20 | 17/20 |
| Mean Ct[2] | 33.2 | NA | 35.0 | NA |
| Standard Deviation (Ct) | 0.8 | NA | 0.9 | NA |

[1]Concentration is presented in RNA copies/µL
[2]Mean Ct reported for dilutions that are ≥95% positive. Calculations only include positive results.
NA not applicable

TABLE 9

CDI SARS-CoV-2 r-RT-PCR Panel using 3-fold
serial dilutions of viral genomic RNA and Takara
One Step PrimeScript ™ RT-PCR Kit

| Genome copies/ rxn | E assay Ct values | | | N2 assay Ct values | | |
|---|---|---|---|---|---|---|
| | Replicate 1 | Replicate 2 | Replicate 3 | Replicate 1 | Replicate 2 | Replicate 3 |
| 2400 | 27.49 | 27.32 | 28.32 | 27.10 | 28.01 | 27.36 |
| 800 | 26.81 | 26.41 | 26.56 | 29.71 | 29.11 | 29.21 |
| 267 | 27.89 | 27.58 | 28.09 | 30.02 | 30.49 | 29.94 |
| 89 | 29.01 | 29.25 | 29.22 | 31.99 | 31.67 | 32.29 |
| 30 | 31.32 | 31.11 | 31.02 | 34.64 | 34.21 | 33.21 |
| 10 | 32.16 | 32.14 | 33.04 | 35.02 | 35.08 | 35.22 |
| 3 | 34.84 | 34.46 | 34.93 | 36.38 | 39.16 | 37.94 |

TABLE 10

CDI SARS-CoV-2 r-RT-PCR Panel using 3-fold
serial dilutions of viral genomic RNA and
Bioline SensiFAST Probe No-ROX One-Step Kit

| Genome copies/ rxn | E assay Ct values | | | N2 assay Ct values | | |
|---|---|---|---|---|---|---|
| | Replicate 1 | Replicate 2 | Replicate 3 | Replicate 1 | Replicate 2 | Replicate 3 |
| 2400 | 26.23 | 25.82 | 26.13 | 27.07 | 26.30 | 26.41 |
| 800 | 30.08 | 30.06 | 29.87 | 30.26 | 30.10 | 30.13 |
| 267 | 31.78 | 31.57 | 31.68 | 32.07 | 32.55 | 31.92 |
| 89 | 33.07 | 33.25 | 33.53 | 33.50 | 33.96 | 33.50 |
| 30 | 35.21 | 33.55 | 37.15 | 35.92 | 37.20 | 35.86 |
| 10 | 38.39 | 37.79 | 37.06 | 39.18 | 38.32 | 39.36 |
| 3 | 38.06 | 37.51 | 37.60 | 38.45 | 39.21 | NA |

TABLE 11

Results of CDI SARS-CoV-2 r-RT-PCR Panel using
3-fold serial dilutions of viral genomic RNA and
Bioline SensiFAST ™ Probe No-ROX One-Step Kit

| Genome copies/ rxn | E assay Ct values | | | N2 assay Ct values | | |
|---|---|---|---|---|---|---|
| | Replicate 1 | Replicate 2 | Replicate 3 | Replicate 1 | Replicate 2 | Replicate 3 |
| 2400 | 26.23 | 25.82 | 26.13 | 27.07 | 26.30 | 26.41 |
| 800 | 30.08 | 30.06 | 29.87 | 30.26 | 30.10 | 30.13 |
| 267 | 31.78 | 31.57 | 31.68 | 32.07 | 32.55 | 31.92 |
| 89 | 33.07 | 33.25 | 33.53 | 33.50 | 339.6 | 33.50 |
| 30 | 35.21 | 33.55 | 37.15 | 35.92 | 37.20 | 35.86 |
| 10 | 38.63 | 32.14 | 33.04 | 35.02 | 35.08 | 35.22 |
| 3 | 35.78 | 37.71 | 37.82 | 38.45 | 39.21 | 40.48 |

TABLE 12

LoD determination results of the CDI SARS-CoV-2
r-RT-PCR Diagnostic Panel using Bioline
SensiFAST ™ Probe No-ROX One-Step Kit

| | Targets | | | | | |
|---|---|---|---|---|---|---|
| | SARS-like coronaviruses (E gene) | | | SARS-CoV-2 (N2 gene) | | |
| RNA Concentration[a] | 4 | 2 | 1 | 4 | 2 | 1 |
| Positives/Total | 24/24 | 22/22 | 20/24 | 24/24 | 22/22 | 23/24 |
| Mean Ct[b] | 33.8 | 34.4 | NA | 36.1 | 36.8 | 37.8 |
| Standard Deviation (Ct) | 0.4 | 0.7 | NA | 0.9 | 1.2 | 0.8 |

[a]Concentration is presented in RNA copies/μL
bMean Ct reported for dilutions that are ≥95% positive. Calculations only include positive results.
NA not applicable Inclusivity Study An inclusivity study may be performed to demonstrate the strains of SARS-CoV-2 that can be detected by the proposed molecular assay. An in silico analysis of published SARS-CoV-2 sequences using the assay's primers and probes may be used. The FDA anticipates that 100% of published SARS-CoV-2 sequences will be detectable with the selected primers and probes.

In silico testing of SARS-CoV-2 N2 assay has been previously performed by the Center for Disease Control and Prevention (CDC). The in silico testing of the present application was performed in a similar manner. The forward primer sequence of SARS-CoV-2 rRT-PCR assay N2 showed high sequence homology to Bat SARS-like coronaviruses. The reverse primer and probe sequences showed no significant homology with human genome, other coronaviruses or human microflora. Thus, when combining primers and probe, there is no prediction of potential false positive rRT-PCR results.

In silico testing of SARS-CoV-2 E assay was also performed. The analysis of the forward and reverse primer and probe sequences of SARS-CoV-2 rRT-PCR E assay showed significant homology only to human SARS coronavirus and bat SARS coronavirus. No significant homology with human genome, other coronaviruses or human microflora was observed that would predict potential false positive rRT-PCR results.

In summary, the CDI SARS-CoV-2 rRT-PCR N2 assay, designed for the specific detection of SARS-CoV-2, showed no significant combined homologies with human genome, other coronaviruses, or human microflora that would predict potential false positive rRT-PCR results. The SARS-CoV-2 rRT-PCR E assay was designed for universal detection of SARS-CoV-2, human SARS coronavirus and bat SARS coronavirus. The SARS-CoV-2 rRT-PCR E assay, as part of the CDI Enhanced COVID-19 Test, showed no significant combined homologies with human genome, other human coronaviruses other than human SARS coronavirus or human microflora that would predict potential false positive rRT-PCR results.

Cross Reactivity

An in silico analysis of the assay primer and probes compared to common respiratory flora and other viral pathogens, listed in the Table 13, may be performed. The FDA defines in silico cross-reactivity as greater than 80% homology between one of the primers/probes and any sequence present in the targeted microorganism.

BLASTn analysis queries of the SARS-CoV-2 rRT-PCR assays primers and probes were performed against public domain nucleotide sequences. The database search parameters were as follows: 1) The nucleotide collection consists of GenBank+EMBL+DDBJ+PDB+RefSeq sequences, but excludes EST, STS, GSS, WGS, TSA; 2) The database is non-redundant. Identical sequences have been merged into one entry, while preserving the accession, GI, title and taxonomy information for each entry; 3) Analysis was performed as of 03/10/2020; 4) The search parameters automatically adjust for short input sequences and the expect threshold is 1000; 5) The match and mismatch scores are 1 and −3, respectively; 6) The penalty to create and extend a gap in an alignment is 5 and 2 respectively.

The N2 assay probe sequence has <78.3% homology to SARS-coronavirus and no significant similarity was found with other organisms listed in Table 14 below. The E assay probe has 88~100% homology with human SARS-CoV and 84~100% homology with bat SARS coronavirus, but no significant similarity with all other organisms listed in Table 14.

TABLE 13

Recommended List of Organisms to be analyzed in silico or by Wet Testing*

| Other high priority pathogens from the same genetic family | High priority organisms likely in circulating areas |
| --- | --- |
| Human coronavirus 229E | Adenovirus (e.g. C1 Ad. 71) |
| Human coronavirus OC43 | Human Metapneumovirus (hMPV) |
| Human coronavirus HKU1 | Parainfluenza virus 1-4 |
| Human coronavirus NL63 | Influenza A & B |
| SARS-coronavirus | Enterovirus (e.g. EV68) |
| MERS-coronavirus | Respiratory syncytial virus |
| | Rhinovirus |
| | Chlamydia pneumoniae |
| | Haemophilus influenzae |
| | Legionella pneumophila |
| | Mycobacterium tuberculosis |
| | Streptococcus pneumoniae |
| | Streptococcus pyogenes |
| | Bordetella pertussis |
| | Mycoplasma pneumoniae |
| | Pneumocystis jirovecii (PJP) |
| | Pooled human nasal wash—to represent diverse microbial flora in the human respiratory tract |
| | Candida albicans |
| | Pseudomonas aeruginosa |
| | Staphylococcus epidermis |
| | Staphylococcus salivarius |

*=For wet testing, concentrations of $10^6$ CFU/ml or higher for bacteria and $10^5$ pfu/ml or higher for viruses is recommended.].

TABLE 14

Analytical Specificity (Cross-Reactivity) of the CDI SARS-CoV-2 r-RT-PCR Panel

| High priority organisms likely in circulating areas | In silico analysis for % identity to target | |
| --- | --- | --- |
| | E assay | N2 assay |
| Human coronavirus 229E | No significant similarity* | No significant similarity* |
| Human coronavirus OC43 | No significant similarity* | No significant similarity* |
| Human coronavirus HKU1 | No significant similarity* | No significant similarity* |
| Human coronavirus NL63 | No significant similarity* | No significant similarity* |

TABLE 14-continued

Analytical Specificity (Cross-Reactivity) of the CDI SARS-CoV-2 r-RT-PCR Panel

| High priority organisms likely in circulating areas | In silico analysis for % identity to target | |
| --- | --- | --- |
| | E assay | N2 assay |
| SARS-coronavirus | 84~100 | <78.3 |
| MERS-coronavirus | No significant similarity* | No significant similarity* |
| Adenovirus (e.g. C1 Ad. 71) | No significant similarity* | No significant similarity* |
| Human Metapneumovirus (hMPV) | No significant similarity* | No significant similarity* |
| Parainfluenza virus 1-4 | No significant similarity* | No significant similarity* |
| Influenza A & B | No significant similarity* | No significant similarity* |
| Enterovirus (e.g. EV68) | No significant similarity* | No significant similarity* |
| Respiratory syncytial virus | No significant similarity* | No significant similarity* |
| Rhinovirus | No significant similarity* | No significant similarity* |
| Chlamydia pneumoniae | No significant similarity* | No significant similarity* |
| Haemophilus influenzae | No significant similarity* | No significant similarity* |
| Legionella pneumophila | No significant similarity* | No significant similarity* |
| Mycobacterium tuberculosis | No significant similarity* | No significant similarity* |
| Streptococcus pneumoniae | No significant similarity* | No significant similarity* |
| Streptococcus pyogenes | No significant similarity* | No significant similarity* |
| Bordetella pertussis | No significant similarity* | No significant similarity* |
| Mycoplasma pneumoniae | No significant similarity* | No significant similarity* |
| Pneumocystis jirovecii (PJP) | No significant similarity* | No significant similarity* |
| Pooled human nasal wash— to represent diverse microbial flora in the human respiratory tract | No significant similarity* | No significant similarity* |
| Candida albicans | No significant similarity* | No significant similarity* |
| Pseudomonas aeruginosa | No significant similarity* | No significant similarity* |
| Staphylococcus epidermis | No significant similarity* | No significant similarity* |
| Staphylococcus salivarius | No significant similarity* | No significant similarity* |

*The probe sequences were blasted against all the exclusive sequences with very low stringency cutoff as defined in above text. No significant similarity was found passing the cutoff and no concerns for cross-reactivity were observed.

Clinical Evaluation

In the absence of known positive samples available for testing, the performance of the assay may be confirmed with a series of contrived clinical specimens by testing a minimum of 30 contrived reactive specimens and 30 non-reactive specimens in a randomized blinded fashion. Contrived reactive specimens may be created by spiking RNA or inactivated virus into leftover individual clinical specimens representing unique patients; the majority of these specimens may be leftover respiratory specimens such as NP swabs, sputum, etc. Twenty of the contrived clinical specimens should be spiked at a concentration of 1×-2× LoD, with the remainder of specimens spanning the assay testing range. The FDA defines the acceptance criteria for the performance as 95% agreement at 1×-2× LoD, and 100% agreement at all other concentrations and for negative specimens.

For the clinical evaluation, 30 non-reactive nasal pharyngeal swabs specimens were used. Another 30 contrived specimens were spiked with viral genomic RNA (Cat #NR-52285) to produce the following viral load: 20 (or 21) with 2×LoD, 5 with 3×LoD, and 5 (or 4) with 4×LoD. These 60 samples were blinded and extracted on the MagNA Pure 24 system. The results are listed in Tables 15 and 16.

TABLE 15

Clinical performance of the CDI SARS-CoV-2
r-RT-PCR Panel using Takara One Step
PrimeScript ™ RT-PCR Kit on nasopharyngeal swabs
Clinical evaluation

| Viral Load | 30 contrived reactive specimens | | | 30 non-reactive specimens | | |
|---|---|---|---|---|---|---|
| | E assay | N2 assay | RP assay | E assay | N2 assay | RP assay |
| 2× LoD | 20/20 | 20/20 | 20/20 | 0/30 | 0/30 | 30/30 |
| 3× LoD | 5/5 | 5/5 | 5/5 | | | |
| 4× LoD | 5/5 | 5/5 | 5/5 | | | |
| | 100% agreement | | | 100% agreement | | |

TABLE 16

Clinical performance of the CDI SARS-CoV-2
r-RT-PCR Panel using Bioline SensiFAST ™
Probe No-ROX One-Step Kit on nasopharyngeal swabs
Clinical evaluation

| Viral Load | 30 contrived reactive specimens | | | 30 non-reactive specimens | | |
|---|---|---|---|---|---|---|
| | E assay | N2 assay | RP assay | E assay | N2 assay | RP assay |
| 2× LoD | 21/21 | 21/21 | 21/21 | 0/30 | 0/30 | 30/30 |
| 3× LoD | 5/5 | 5/5 | 5/5 | | | |
| 4× LoD | 4/4 | 4/4 | 4/4 | | | |
| | 100% agreement | | | 100% agreement | | |

A method for preparing the assays in the detection panel is also provided. The assays for use in the detection panel are prepared in a master mix. The master mix may be prepared for each assay according to Tables 17-20. The master mix preparation is dependent on the RT-PCR kit that is used for testing. In particular, the inventors have found that One Step PrimeScript™ RT-PCR Kit sold by Takara and Sensi-FAST™ Probe No-ROX One-Step Kit sold by Bioline are most effective when used with the master mix of the present application.

Once the master mix is prepared, the RT-PCR kit may be prepared. If One Step PrimeScript™ RT-PCR Kit is used, the kit should be prepared as described using the assays in Tables 17 and 18. If SensiFAST™ Probe No-ROX One-Step Kit is used, the kit should be prepared as described using the assays in Tables 19 and 20.

a. One Step PrimeScript™ RT-PCR Kit (Perfect Real Time) has labeled each component and assigned tube number as 1, 2, 3, 4, 5, 6. Tubes 5 & 6 are not used for assay set up.

b. The total volume of each reaction is 20 uL (15 ul master mix+5 ul RNA).

c. To prepare enough master mix for 16 reactions ("rxn"), time 17 to each component in the master mix as indicted in the below table.

TABLE 17

N2 & RP assay set up

| Takara tube no. | Reagent | μL/reaction |
|---|---|---|
| ① | 2X One Step RT-PCR Buffer III | 10 |
| ② | TaKaRa Ex Taq HS (5 U/μl) | 0.4 |
| ③ | PrimeScript RT enzyme Mix II | 0.4 |
| ④ | RNase Free dH2O | 3 |
| | Combined Primer/Probe Mix | 1.2 |
| | Total master mix Volume | 15 |
| | RNA | 5 |

TABLE 18

E assay set up

| Takara tube no. | Reagent | μL/reaction |
|---|---|---|
| ① | 2X One Step RT-PCR Buffer III | 10 |
| ② | TaKaRa Ex Taq HS (5 U/μl) | 0.4 |
| ③ | PrimeScript RT enzyme Mix II | 0.4 |
| ④ | RNase Free dH2O | 1.8 |
| | Combined Primer/Probe Mix | 2.4 |
| | Total master mix Volume | 15 |
| | RNA | 5 |

TABLE 19

N2 & RP assay set up

| Reagent | μL/reaction |
|---|---|
| 2x SensiFAST Probe No-ROX One-Step Mix | 10 |
| Reverse transcriptase | 0.2 |
| RiboSafe RNase Inhibitor | 0.4 |
| RNase Free dH2O | 3.2 |
| Combined Primer/Probe Mix | 1.2 |
| Total master mix Volume | 15 |
| RNA | 5 |

TABLE 20

E assay set up

| Reagent | μL/reaction |
|---|---|
| 2x SensiFAST Probe No-ROX One-Step Mix | 10 |
| Reverse transcriptase | 0.2 |
| RiboSafe RNase Inhibitor | 0.4 |
| RNase Free dH2O | 2 |
| Combined Primer/Probe Mix | 2.4 |
| Total master mix Volume | 15 |
| RNA | 5 |

Once the master mix is prepared for the respective RT-PCR kit to be used, the diagnostic plate may be set up as follows. The plate set up is independent of RT-PCR kit, meaning that the plate set up applies for both One Step PrimeScript™ RT-PCR Kit and SensiFAST™ Probe No-ROX One-Step Kit.

d. Load 15 ul of master mix to wells as defined by the plate map;

e. Add 5 ul of ribonucleic acid ("RNA") to each well as defined by the plate map;

f. Close up the caps and transfer samples onto mic cycler.

| | N2↓ 1 | E↓ 2 | RP↓ 3 | N2↓ 4 | E↓ 5 | RP↓ 6 |
|---|---|---|---|---|---|---|
| A | P1 | P1 | P1 | P9 | P9 | P9 |
| B | P2 | P2 | P2 | P10 | P10 | P10 |
| C | P3 | P3 | P3 | P11 | P11 | P11 |
| D | P4 | P4 | P4 | P12 | P12 | P12 |
| E | P5 | P5 | P5 | HSC | HSC | HSC |
| F | P6 | P6 | P6 | NEC[a] | NEC[a] | NEC[a] |
| G | P7 | P7 | P7 | PC | PC | PC |
| H | P8 | P8 | P8 | NTC | NTC | NTC |

[a]NEC: negative extraction control

The plate is then transferred to a mic qPCR cycle for analysis and the rRT-PCR is run. The thermal cycling conditions may be set based on the RT-PCR kit used. If the One Step PrimeScript™ RT-PCR Kit is used, the thermal cycling conditions in Table 21 may be used for the assay. If the SensiFAST™ Probe No-ROX One-Step Kit is used, the thermal cycling conditions in Table 22 may be used for the assay.

g. Turn on mic cycler and the computer;
  h. Open up the micPCR software, and make sure the instrument is recognized by the computer;
  i. Create new run using assay "CDI-COVID19" (Takara kit based) or "Bioline-SARS-CoV2" (Bioline kit based);
  j. Input sample name and select sample type as "unknown," "NTC," or "positive control" as appropriate;
  k. Assign group (N2, E, RP) to each sample;
  l. Start the run.

TABLE 21

CDI-COVID19 thermal cycling condition

| Stage 1: Reverse transcription | |
|---|---|
| 42° C. 5 min | ×1 cycle |
| 95° C. 10 sec | |
| Stage 2: PCR reaction | |
| 95° C. 5 sec | ×45 cycles |
| 58° C. 20 sec | |

TABLE 22

Bioline-SARS-CoV2 thermal cycling condition

| Stage 1: Reverse transcription | |
|---|---|
| 45° C. 10 min | ×1 cycle |
| 95° C. 2 sec | |
| Stage 2: PCR reaction | |
| 95° C. 5 sec | ×45 cycles |
| 58° C. 20 sec | |

It will be understood that the foregoing examples and explanation are for illustrative purpose only and that in view of the instant disclosure various modifications of the present invention will be self-evident to those skilled in the art and are to be included within the spirit and purview of this application and the scope of the claims.

What is claimed is:

1. A method for detecting a novel coronavirus, severe acute respiratory syndrome-Coronavirus-2 (SARS-CoV-2), in a sample, consisting of:
   a) collecting a sample suspected of comprising the novel coronavirus;
   b) analyzing by polymerase chain reaction (PCR) at least a first portion of the sample for one region in a SARS-CoV-2 nucleocapsid (N) gene using a SARS-CoV-2 specific N2 assay, the N2 assay including a PCR primer including SEQ ID NO: 1, an RT & PCR primer including SEQ ID NO:2, and a PCR probe including SEQ ID NO:3;
   c) analyzing by PCR at least a second portion of the sample for universal detection of a SARS-like coronavirus envelope (E) gene using an E assay, the E assay including a PCR primer including SEQ ID NO:4, an RT & PCR primer including SEQ ID NO:5, and a PCR probe including SEQ ID NO:6;
   d) analyzing by PCR at least a third portion of the sample to detect human RNase P (RP) using a RP assay as internal control, the RP assay including a PCR primer including SEQ ID NO:7, an RT & PCR primer including SEQ ID NO:8, and a PCR probe including SEQ ID NO:9; and
   e) combining the three assays and evaluating results of the N2, the E and the RP assays to determine a presence or an absence of the novel coronavirus in the sample, wherein:
   when the SARS-CoV-2 specific N2 assay is positive, then SARS-CoV-2 is determined present in the sample;
   when the SARS-CoV-2 specific N2 assay is negative and the E assay is positive, then SARS-CoV-2 is presumed present in the sample;
   when the SARS-CoV-2 specific N2 assay and the E assay are negative and the RP assay is positive, then SARS-CoV-2 is determined absent in the sample;
   when all of the SARS-CoV-2 specific N2 assay, the E assay, and the RP assay are negative, then the result of the N2, E, and RP assays is invalid.

2. The method of claim 1, wherein the N2 assay is novel coronavirus ("nCoV") specific.

3. The method of claim 1, wherein the E assay probe is capable of universal detection of SARS-like coronaviruses.

4. The method of claim 1, wherein the sample is collected from at least one of nasopharyngeal, or oropharyngeal, or anterior nasal, or mid-turbinate nasal, or upper respiratory specimens, or blood, urine or stool.

5. A method for detecting a novel coronavirus, severe acute respiratory syndrome-Coronavirus-2 (SARS-CoV-2) in a sample, consisting of:
   preparing a PCR master mix for each of a combination of assays wherein the combination of assays consists of a first assay that is novel coronavirus ("nCoV") specific; a second assay capable of universal detection of SARS-like coronaviruses; and a third assay that is an internal control;
   loading 15 μL of the master mix to each of a plurality of wells, wherein the wells are defined by a plate map;
   adding 5 μL of ribonucleic acid ("RNA") to each well as defined by the plate map; transferring the sample to a mic cycler; and running the mic cycler;
   creating a new run of PCR that includes a thermal cycling condition;
   selecting a sample type, wherein the sample type is (1) unknown, (2) no template negative control (NTC), or (3) positive control;

assigning a group to the sample, wherein the group is analyzed by (1) the first assay, (2) the second assay, or (3) the third assay; and running the mic cycler;
   wherein the first assay consists of an N2 assay wherein the N2 assay is using a PCR primer including SEQ ID NO: 1, an RT & PCR primer including SEQ ID NO:2 and a PCR probe including SEQ ID NO:3, and the second assay consists of an E assay wherein the E assay is using a PCR primer including SEQ ID NO:4, an RT & PCR primer including SEQ ID NO:5 and a PCR probe including SEQ ID NO:6, and the third assay consists of an RP assay wherein the RP assay is using a PCR primer including SEQ ID NO:7, an RT & PCR primer including SEQ ID NO:8 and a PCR probe including SEQ ID NO:9; and
   wherein evaluation of the combination of the N2, the E and the RP assays results determine a presence or an absence of the novel coronavirus in the sample, and wherein:
   when the SARS-CoV-2 specific N2 assay is positive, then SARS-CoV-2 is determined present in the sample;
   when the SARS-CoV-2 specific N2 assay is negative and the E assay is positive, then SARS-CoV-2 is presumed present in the sample;
   when the SARS-CoV-2 specific N2 assay and the E assay are negative and the RP assay is positive, then SARS-CoV-2 is determined absent in the sample; and
   when all of the SARS-CoV-2 specific N2 assay, the E assay, and the RP assay are negative, then the result of the N2, E, and RP assays is invalid.

6. The method of claim 5, wherein the master mix for the RP assay and N2 assay is further defined as (1) a first premix containing at least a reaction buffer and dNTP mixture, (2) a hot start PCR enzyme that includes at least a Taq antibody (5 U/μl), (3) a second premix containing at least a reverse transcriptase, a ribonuclease and a stabilizing agent, (4) RNase Free dH2O, and (5) Combined Primer/Probe Mix.

7. The method of claim 6, wherein the master mix for the RP assay and the N2 assay has amounts of at least 10 μL/reaction of the first premix, 0.4 μL/reaction of the hot start PCR enzyme (5 U/μl), 0.4 μL/reaction of the second premix, 3 μL/reaction of RNase Free dH2O, and 1.2 μL/reaction of Combined Primer/Probe Mix.

8. The method of claim 5, wherein the master mix for the E assay is further defined as (1) a first premix containing at least a reaction buffer and dNTP mixture, (2) a hot start PCR enzyme that includes at least a Taq antibody (5 U/μl), (3) a second premix containing at least a reverse transcriptase, a ribonuclease and a stabilizing agent, (4) RNase Free dH2O, and (5) E Probe Mix.

9. The method of claim 8, wherein the master mix for the E assay has amounts of at least 10 μL/reaction of the first premix, 0.4 μL/reaction of the hot start PCR enzyme (5 U/μl), 0.4 μL/reaction of the second premix, 1.8 μL/reaction of RNase Free dH2O, and 2.4 μL/reaction of E Probe Mix.

10. The method of claim 5, wherein the plate map is further defined as:

|   | N2 1 | E 2 | RP 3 | N2 4 | E 5 | RP 6 |
|---|------|-----|------|------|-----|------|
| A | P1 | P1 | P1 | P9 | P9 | P9 |
| B | P2 | P2 | P2 | P10 | P10 | P10 |
| C | P3 | P3 | P3 | P11 | P11 | P11 |

-continued

|   | N2 1 | E 2 | RP 3 | N2 4 | E 5 | RP 6 |
|---|------|-----|------|------|-----|------|
| D | P4 | P4 | P4 | P12 | P12 | P12 |
| E | P5 | P5 | P5 | HSC | HSC | HSC |
| F | P6 | P6 | P6 | NEC | NEC | NEC |
| G | P7 | P7 | P7 | PC | PC | PC |
| H | P8 | P8 | P8 | NTC | NTC | NTC | wherein N2, E, and RP are the assays, wherein the N2 assay is using a PCR primer of sequence SEQ ID NO:1, an RT & PCR primer of sequence SEQ ID NO:2 and a PCR probe of sequence SEQ ID NO:3, and the E assay is using a PCR primer of sequence SEQ ID NO:4, an RT & PCR primer of sequence SEQ ID NO:5 and a PCR probe of sequence SEQ ID NO:6, and the RP assay is using a PCR primer of sequence SEQ ID NO:7, an RT & PCR primer of sequence SEQ ID NO:8 and a PCR probe of sequence SEQ ID NO:9, A . . . H are vertical locators for wells;

1 . . . 6 are horizontal locators for wells;

P1 . . . P12 are combined primer/probe mix,

HSC is a human RNA extract

NEC is a negative extraction control

PC is a positive control, and

NTC is a no template control.

11. The method of claim 5, wherein the thermal cycling condition is further defined as a first stage and a second stage, the first stage is run at 42° C. for 5 minutes for one cycle and the second stage is run at 95° C. for 5 seconds and 58° C. for 20 seconds for 45 cycles.

\* \* \* \* \*